(12) United States Patent
Kucklick

(10) Patent No.: US 8,585,773 B1
(45) Date of Patent: Nov. 19, 2013

(54) METHOD AND DEVICES FOR IMPLANTATION OF BIOLOGIC CONSTRUCTS

(75) Inventor: Theodore R. Kucklick, San Jose, CA (US)

(73) Assignee: Cannuflow, Inc., San Jose, CA (US)

( * ) Notice: Subject to any disclaimer, the term of this patent is extended or adjusted under 35 U.S.C. 154(b) by 175 days.

(21) Appl. No.: 13/088,327

(22) Filed: Apr. 15, 2011

Related U.S. Application Data

(60) Provisional application No. 61/324,746, filed on Apr. 15, 2010.

(51) Int. Cl.
*A61F 2/02* (2006.01)
*A61B 17/08* (2006.01)

(52) U.S. Cl.
USPC ........................................ 623/23.72; 606/151

(58) Field of Classification Search
USPC .................. 606/151, 213; 600/29, 30, 37; 623/23.72

See application file for complete search history.

(56) References Cited

U.S. PATENT DOCUMENTS

| | | | | |
|---|---|---|---|---|
| 5,176,692 | A | * | 1/1993 | Wilk et al. ...................... 606/151 |
| 5,366,460 | A | * | 11/1994 | Eberbach ....................... 606/151 |
| 5,370,650 | A | * | 12/1994 | Tovey et al. ................... 606/151 |
| 7,608,091 | B2 | * | 10/2009 | Goldfarb et al. .............. 606/151 |

* cited by examiner

*Primary Examiner* — Julian W Woo
(74) *Attorney, Agent, or Firm* — Susan L. Crockett, Esq.; Crockett & Crockett, PC

(57) ABSTRACT

Methods and devices for prepping and delivering a biologic construct repair for shoulder and joint surgery into an arthroscopic workspace.

8 Claims, 6 Drawing Sheets

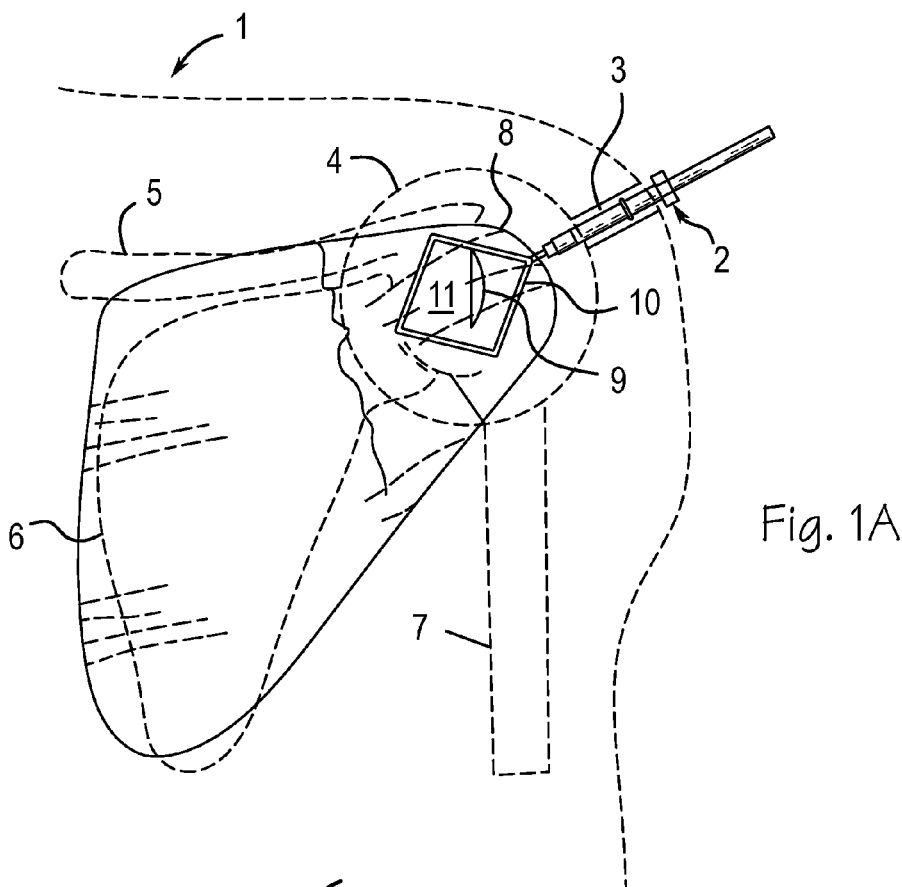
Fig. 1A
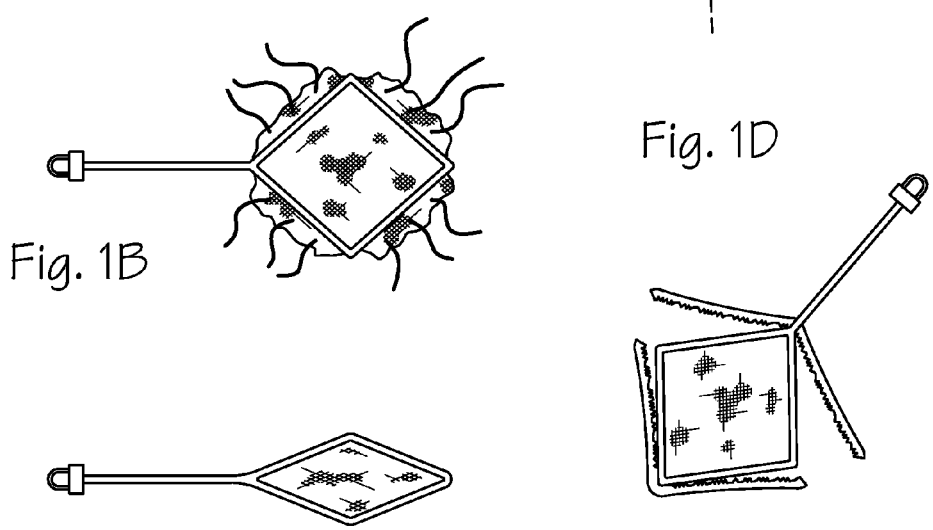
Fig. 1D
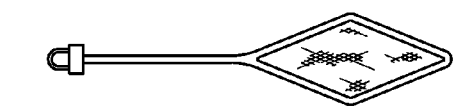
Fig. 1B
Fig. 1C

Fig. 5A
Fig. 5B
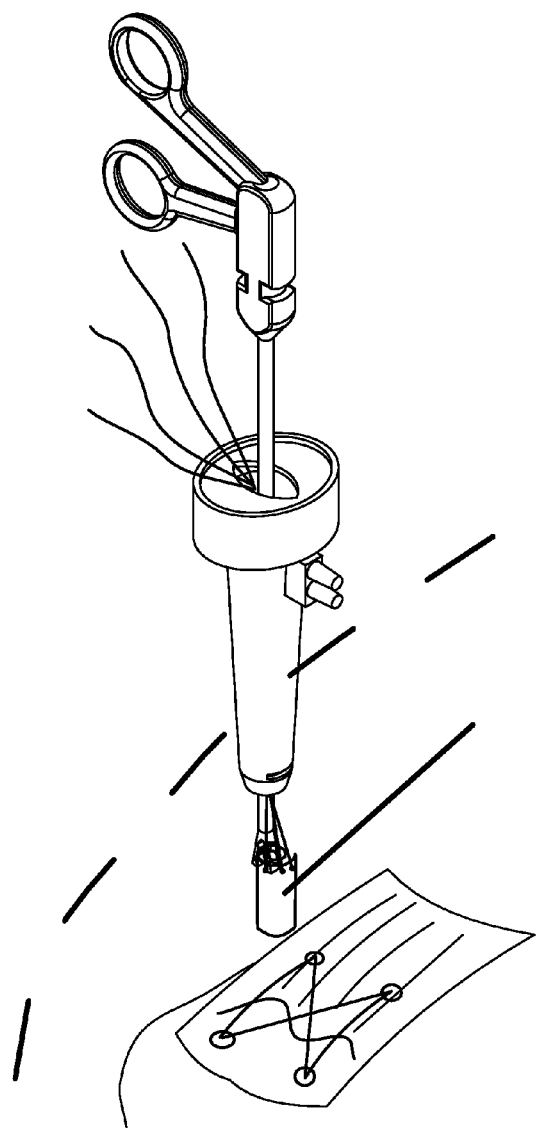
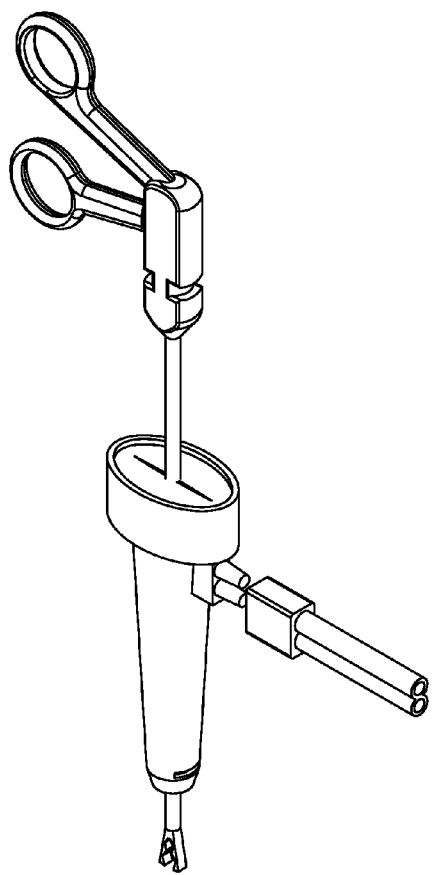

METHOD AND DEVICES FOR IMPLANTATION OF BIOLOGIC CONSTRUCTS

RELATED APPLICATIONS

This application claims priority to copending U.S. Provisional Patent Application 61/324,746 Apr. 15, 2010.

FIELD OF THE INVENTIONS

The inventions described below relate to the field of arthroscopic surgery and more specifically to implantation of biologic constructs.

BACKGROUND OF THE INVENTIONS

Biologic constructs, which include "regenerative tissue matrices" "acellular tissue matrices" or "collagen scaffolds" and other such substances, are small sheets or disks of flexible, engineered biomaterial, such as collagen or fibrin, decellularized dermal matrix crosslinked and sterilized xenograft tissues, and "platelet-rich-plasma" patches sometimes totally devoid of living cell material and sometimes loaded with active adjuncts such as biologic growth factors. Biologic constructs may also be tissue-engineered from mesenchymal stem cells. For the purposes of this application, the term biologic construct refers to any sheet-like or disc-like configuration of regenerative tissue matrix, acellular tissue matrices or collagen scaffolds, or similar materials suitable for placement within the body to promote healing.

Biologic constructs and implants are growing rapidly in popularity for the repair of joint pathologies. Biologic constructs may be a new alternative for carpal arthroplasty in patients with clinical conditions such as osteonecrosis. Biologic constructs are a family of biologically derived implants to promote tissue growth or to patch and repair tissue defects and tears. These include the repair of arthritic cartilage, the joining of tendons to bone and the bridging of degenerated rotator cuff in the shoulder. Biologic constructs, and graft material such as platelet rich fibrin membrane, acellular dermal allograft, (MTF) and xenograft materials (Pegasus Biologics) and graft patches (Wright Medical Graftjacket) have enabled the reconstruction and treatment of previously untreatable and irreparable musculoskeletal injuries and pathologies. Biologic constructs now occupy an increasingly important place in the orthopedic surgeons armamentarium.

One of the key problems with biologic constructs is that the delivery instrumentation has not kept pace with advances in these implants. For example, fluid seals that work effectively hold fluid while passing sutures and metal instruments are not able to pass these biologic constructs without tearing and damage. This can render the construct useless, and add significantly to the cost of the case, as these implants can be fragile as well as expensive. A damaged implant can result in several hundred dollars of added expense.

In addition to these constructs being soft, floppy, and prone to damage from tearing, suture management is very difficult, both during the preparation of the implant outside the patient as well as managing the implant and sutures when the implant is manipulated and attached in the joint. Currently an implant construct is hand-held with hemostats by an assistant while the graft is prepared with sutures.

An important clinical need exists to make these biologic constructs easier to prepare, handle, deliver, and implant so that the potential of these important advances in biologics can be fully realized.

SUMMARY

The present invention solves the most important problems with biologic constructs, that is, preparation of the graft prior to insertion into the patient, the ability to pass the fragile implant into the joint space without damaging or tearing the implant, and being able to manipulate the soft and floppy implant within the joint space. All of these improvements to the delivery instrumentation will reduce costs, reduce risks to the patient, and greatly improve the speed and success of the procedure.

There are four basic components to the system: 1) having a frame to prepare the graft outside the body, 2) having a seal system that allows passage of a large, soft construct without damage, and has the ability to be fluid-tight 3) a means of deploying and orienting the construct within the body and 4) a means of managing the sutures.

There are two basic procedures being addressed: one is to bridge a massively retracted and irreparable rotator cuff tear, (with a sheet of repair material) and the other is to augment a tendon to bone repair in order to promote healing of tendon to bone (platelet rich patch).

BRIEF DESCRIPTION OF THE DRAWINGS

FIGS. 1A, 1B, 1C, and 1D illustrate the kite.
FIGS. 5A and 5B illustrates the coin purse cannula.

DETAILED DESCRIPTION OF THE INVENTIONS

Figure 2A:
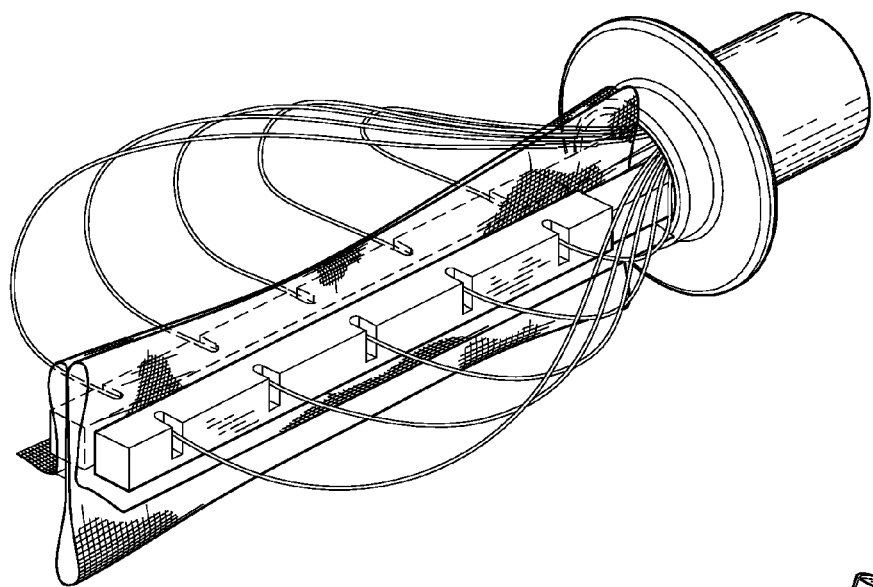
FIGS. 2A and 2B illustrate the cage.
Figure 2B:
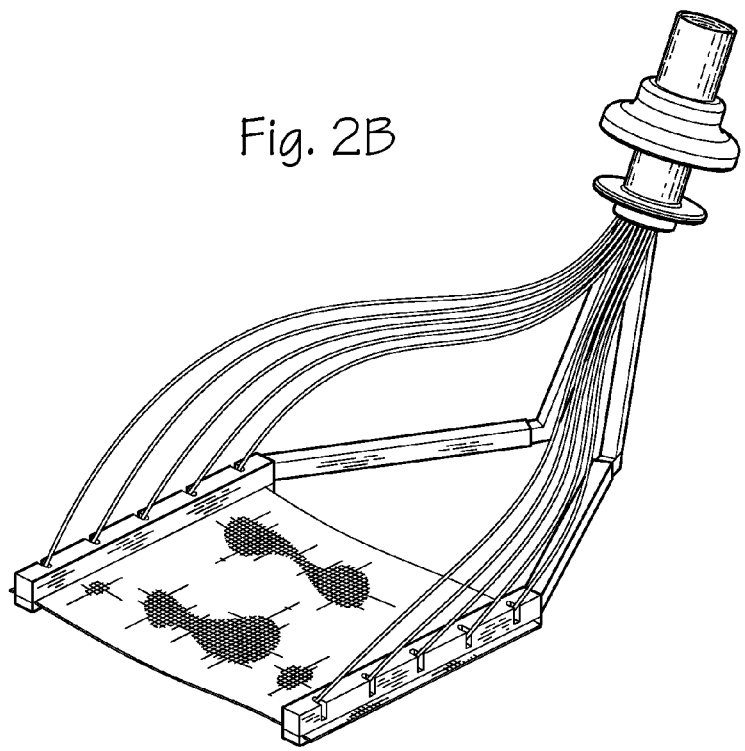

The methods and devices described below provide for convenient prepping and delivering a biologic construct repair for shoulder and joint surgery into an arthroscopic workspace. There are four basic components to the system: 1) a frame to prepare the graft outside the body, 2) a seal system that allows passage of a large, soft construct without damage, and has the ability to be fluid-tight 3) a means of deploying and orienting the construct within the body and 4) a means of managing the sutures.

FIGS. 1B, 1C, 1D, and 1A show a "kite" graft repair and delivery system. The "kite" is a loop of superelastic or shape memory nickel-titanium with clamps that hold the construct, and is delivered through a tube and deployed inside the body. This design calls for a nitinol or hinged frame with integrated clamps that allow the biologic construct sheet to be folded, and delivered either through a surgical wound portal, or a cannula device to a site to be repaired, such as a torn rotator cuff in a shoulder. This design allows the graft to be prepped outside the body with sutures, and held in a collapsible frame for handling, and to be deployed within a body. The frame has a feature to allow it to be releasably attached to a handle for insertion through a surgical wound or cannula.

As shown in FIG. 1A, in use, the surgeon delivers the biologic construct to a joint within the body of a patient 1 by creating an arthroscopic workspace 4 around the joint and inserting a cannula 3 through the skin of the patient proximate the arthroscopic workspace. A sheet of biologic construct 11 is provided. A collapsible first frame 10 is configured to hold the sheet of biologic construct 11. The surgeon attaches the sheet of biologic construct to the collapsible first frame, collapses the collapsible first frame with the sheet attached such that the frame and sheet fit, in a collapsed configuration, through the cannula. The surgeon inserts the collapsible first frame and sheet, in the collapsed configuration, through the cannula 3 and into the arthroscopic workspace; expanding the collapsible first frame and sheet within the workspace and positioning the sheet proximate an intended site of implantation; releasing the sheet from the collapsible first frame, collapsing the collapsible first frame and removing the collapsible first frame from the workspace; and securing the sheet to body tissue within the workspace.

The delivery device shown in FIG. 1A through 1D comprises an elongate insertion portion 2 having a proximal end and a distal end adapted for insertion into an arthroscopic workspace through a cannula or small incision proximate the workspace; a grasping member disposed on the distal end of the elongate insertion portion 2, wherein the grasping member comprises a collapsible frame comprising a first frame member which is collapsible from a wide configuration which tensions the sheet into a substantially flat configuration to a narrow configuration adapted for insertion into arthroscopic workspace through the cannula or small incision proximate the workspace. The grasping member further comprise a clamping member adapted to trap the sheet between the clamping member and the first frame.

The delivery device may also comprise an elongate insertion portion 2 having a proximal end and a distal end adapted for insertion into an arthroscopic workspace through a cannula or small incision proximate the workspace and a grasping member disposed on the distal end of the elongate insertion portion, with the grasping member comprising a collapsible frame comprising a first frame member which is collapsible from a wide configuration which tensions the sheet into a substantially flat configuration to a narrow configuration adapted for insertion into arthroscopic workspace through the cannula or small incision proximate the workspace. The grasping member further comprises a clamping member adapted to trap the sheet between the clamping member and the first frame.

The first frame member can be rectangular, and attached to the elongate insertion portion at a corner of frame. The first frame member can be rectangular, and attached to the elongate member at a corner of frame, and the clamping member also comprises an articulating arm that may be selectively apposed to a side of the rectangular frame to trap the sheet between the clamping member and the frame. The first frame member can be rectangular and attached to the elongate member at a corner of frame and be hinged at the remaining three corners of the frame. The first frame member can be rectangular comprising a superelastic material. The first frame member can also be circular or elliptical.

Another embodiment is where the holders for the construct are "legs" made of a preshaped spring material. This embodiment is shown in 2A and 2B. Inserted in the tube in a closed position, implant is folded up on the end. At the surgical site, spreads open inside, for example, the shoulder, at the surgical site. The legs spring open, which puts the implant in an open unfolded position. This device comprises an elongate insertion portion having a proximal end and a distal end adapted for insertion into an arthroscopic workspace through a cannula or small incision proximate the workspace and a pair of grasping jaws disposed on the distal end of the insertion portion. The pair of grasping jaws pivotably engaged with the elongate insertion portion such that they may be moved in away from each other to an open configuration and tension the biologic construct to a flat configuration, and closed in apposition to each other to fold the biologic construct between the pair of grasping jaws. Also, each of the pair of grasping jaws is operable to grasp the biologic construct and release the biologic construct. At least one of the grasping jaws includes a plurality of slots adapted to accept a suture segment attached to the biologic construct, as shown in FIG. 2A.

The grasping jaws can be made of a superelastic or resilient material biased to the open configuration, such that the grasping jaws may be forced in apposition to each other to fit into a cannula and thereafter superelastically or resiliently open upon exit from a distal end of the cannula.

Figure 3A:
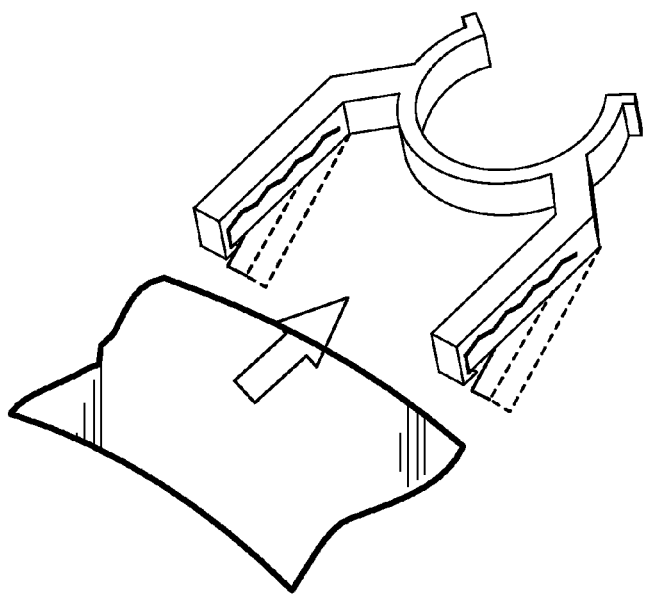
FIGS. 3A and 3B illustrate the implant frame and clamp.
Figure 3B:
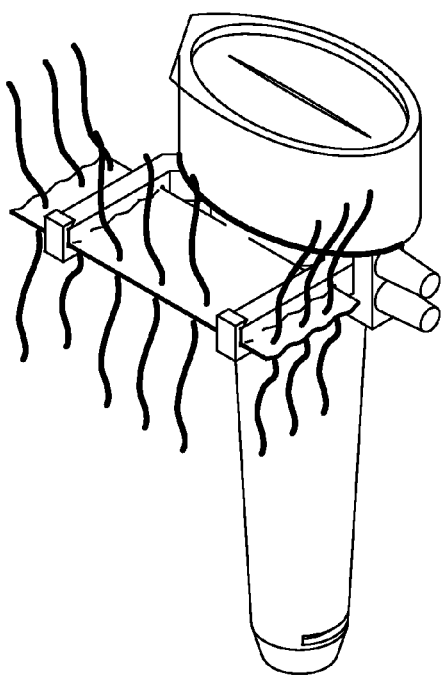

FIGS. 3A and 3B show an implant graft holder 1. The graft holder 1 holds a tissue construct patch 2 in place for suturing. Currently, an assistant has to hold the patch in the air with two hemostats. The clamp 3 and frame 4 are detachable from the cannula for graft prep, and to easily removable when the suturing procedure is complete. The implant frame 4 holds the implant grafts 2 for the surgeon while the surgeon places the sutures in the graft. The frame removably clips to cannula, as shown in FIGS. 3A and 3B. The implant 2 clamps into the frame. The frame 4 is flexible and generally made of injection moldable plastic or other suitable material. The frame holds the implant in place for easy suture placement.

A second frame adapted to hold the sheet to the cannula, securing the sheet to the second frame, securing a number of suture segments to the sheet while the sheet is secured to the second frame, and thereafter transferring the sheet to the collapsible first frame and performing the inserting step; securing the sheet to body tissue within the workspace with the suture segments with an interrupted suture technique.

Figure 4A:
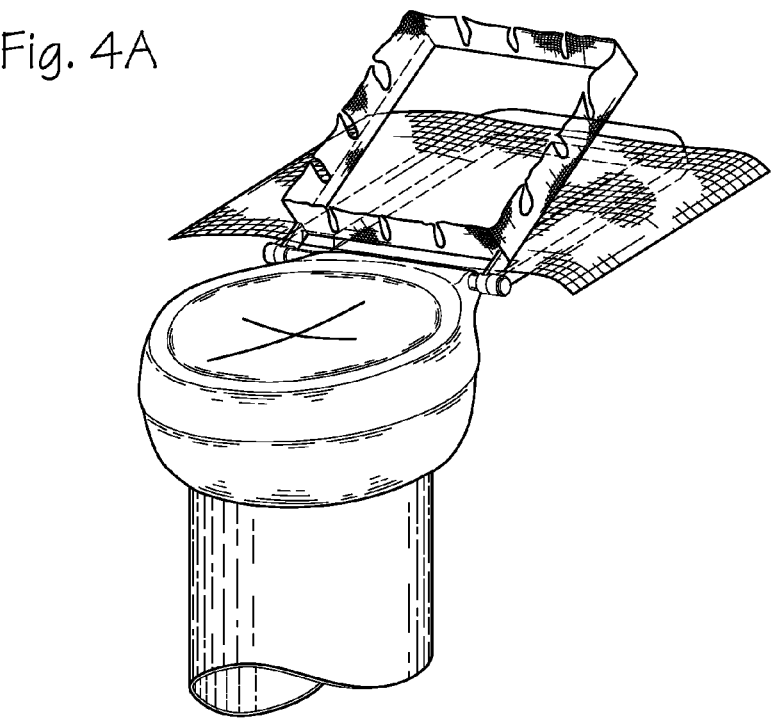
FIGS. 4A and 4B illustrate the suture management accessory.
Figure 4B:
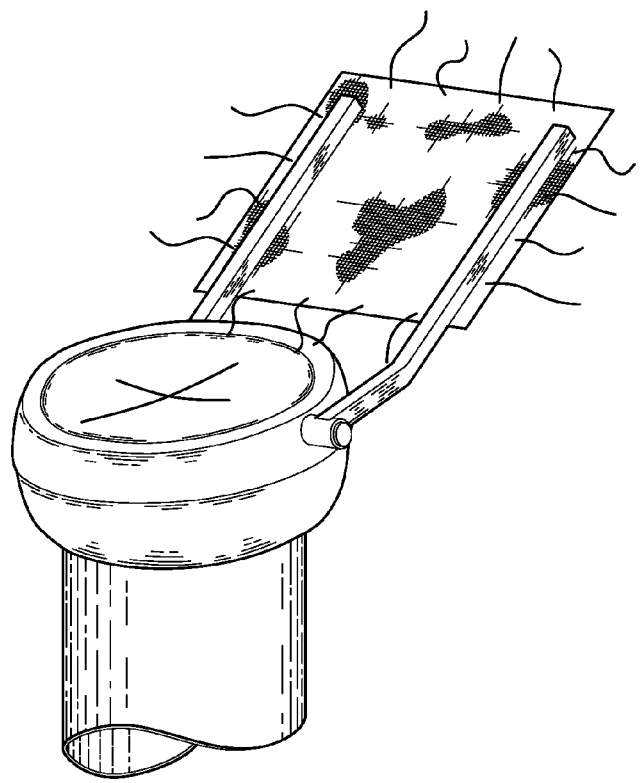

FIGS. 4A and 4B illustrate an accessory that allows a biologic construct sheet to be secured in a flat form, to be prepared with sutures for sewing into a defect, and a means for these sutures to be sorted and managed to enable efficient knot-tying and prevent tangling of the sutures as the prepared construct is delivered into the surgical space and secured into the tissue defect. Detachable allows back table prep and transfer.

FIGS. 5A and 5B show a cannula that provides for a way to pass a larger object through a cannula. Traditional septum seals are too tight for this. The cannula 5 opening is oval in shape and made of a flexible material that when pinched, opens the slit 6. When the surgeon lets go, the slit seals back up again. This provides for a way to pass larger or fragile items like biologic graft patches and gelatinous platelet blob implants into the surgical site. As shown in FIG. 5B, the grasper is inserted into the top of the cannula, with the implant attached with the grasper, the grasper is inserted into the cannula and the graft patch is delivered to the rotator cuff at the repair site.

The "coin purse" seal shown in FIGS. 5A and 5B are part of a system that allows a large, floppy biologic construct to be prepared outside the patient, passed through a cannula, and arranged in place inside a body arthroscopically. The "coin purse" cannula is one embodiment that allows passage of a large soft object like a biologic sheet, and still allows the seal to close and prevent the leakage of fluid from the joint. Methods and devices for managing and isolating sutures are disclosed also.

Coin purse cannula seal for passing larger objects into the joint, e.g. biologics and tissue implants. When closed, holds fluid seal and distension. Modular fluid tubeset connector. Squeeze to open, like a coin purse, release to close and re-seal. Septum opens to allow passage of large implant constructs that do not fit thru conventional cannulae. Biologic construct or implant hanging off the bottom. Endoscopic tissue repair site, e.g. rotator cuff repair.

Figure 6A:
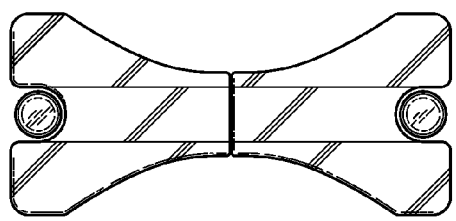
FIGS. 6A, 6B, and 6C illustrate the sphincter seal.
Figure 6B:
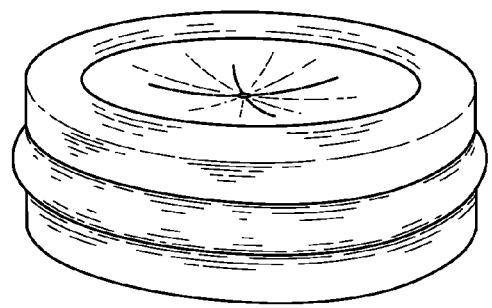
Figure 6C:
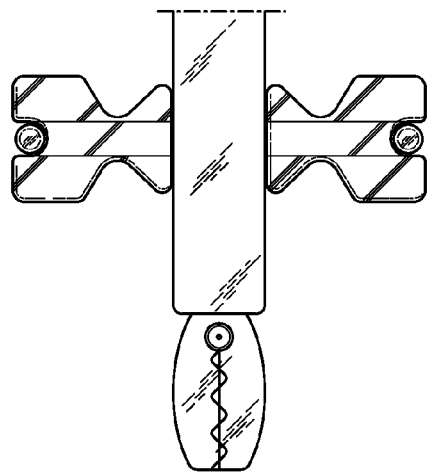

Another seal design is shown in FIGS. 6A, 6B, and 6C. This seal acts like a sphincter. The seal has a low durometer of 10-30 A with a stiffer o-ring of 40-80 A. The center seal stretches while the O-ring pulls the seal closed when the instrument is removed. This dual-compliance system allows easy passage of instrument and sealing of septum in "sphincter-like" manner. It is a "dual state" seal that is tight and leak resistant when the O-ring is in place, and more compliant when the O-ring is slipped out of its groove. The O-ring may be slipped back in the groove for a tighter seal once the implant is passed through. This also allows passage of large, soft implants without damaging the implant, and allows returning to a fluid-tight seal state.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method of delivering a biologic construct to a joint within the body of a patient, said method comprising:
   creating an arthroscopic workspace around the joint and inserting a cannula through the skin of the patient proximate the arthroscopic workspace;
   providing a sheet of biologic construct;
   providing a collapsible first frame configured hold the sheet;
   attaching the sheet to the collapsible first frame
   collapsing the collapsible first frame with the sheet attached such that the frame and sheet fit, in a collapsed configuration, through the cannula;
   inserting the collapsible first frame and sheet, in the collapsed configuration, through the cannula and into the arthroscopic workspace;
   expanding the collapsible first frame and sheet within the workspace and positioning the sheet proximate an intended site of implantation;
   releasing the sheet from the collapsible first frame, collapsing the collapsible first frame and removing the collapsible first frame from the workspace; and
   securing the sheet to body tissue within the workspace;
   wherein prior to inserting the collapsible first frame and sheet, the method includes:
   securing a second frame adapted to hold the sheet to the cannula, securing the sheet to the second frame, securing a number of suture segments to the sheet while the sheet is secured to the second frame, and thereafter transferring the sheet to the collapsible first frame, and wherein the suture segments are used to secure the sheet to body tissue within the workspace with an interrupted suture technique.

2. A device for delivering a sheet of biologic construct, said device comprising:
   an elongate insertion portion having a proximal end and a distal end adapted for insertion into an arthroscopic workspace through a small incision proximate the workspace;
   a grasping member having a proximal end and a distal end, said grasping member proximal end disposed on the distal end of the insertion portion, said grasping member comprising a collapsible frame comprising a first frame member which is collapsible from a wide configuration which is configured to tension the sheet into a substantially flat configuration to a narrow configuration adapted for insertion into the arthroscopic workspace through the small incision proximate the workspace, said grasping member further comprising a first clamping member disposed at the proximal end of the grasping member and a second clamping member disposed at the distal end of the grasping member, said clamping members adapted to trap the sheet between said clamping members and the first frame.

3. A device for delivering a sheet of biologic construct, said device comprising:
   an elongate insertion portion having a proximal end and a distal end adapted for insertion into an arthroscopic workspace through a cannula;
   a grasping member having a proximal end and a distal end, said grasping member proximal end disposed on the distal end of the insertion portion, said grasping member comprising a collapsible frame comprising a first frame member which is collapsible from a wide configuration which is configured to tension the sheet into a substantially flat configuration to a narrow configuration adapted for insertion into the arthroscopic workspace through the cannula, said grasping member further comprising a first clamping member disposed at the proximal end of the grasping member and a second clamping member disposed at the distal end of the grasping member, said clamping members adapted to trap the sheet between said clamping members and the first frame.

4. The device of claim 3, wherein the first frame member is rectangular, and is attached to the elongate member at a corner of frame.

5. The device of claim 3, wherein the first frame member is circular or elliptical.

6. The device of claim 3, wherein the first frame member is rectangular, and is attached to the elongate member at a corner of the frame, and the clamping members further comprise a first articulating arm and a second articulating arm that may be selectively apposed to a side of the rectangular frame to trap the sheet between the clamping members and the frame.

7. The device of claim 3, wherein the first frame member is rectangular, and is attached to the elongate member at a corner of frame and is hinged at the remaining three corners of the frame.

8. The device of claim 3, wherein the first frame member is rectangular, and comprising a superelastic material.

* * * * *